United States Patent [19]
Corrigan et al.

[11] Patent Number: 5,840,703
[45] Date of Patent: Nov. 24, 1998

[54] PHASE TRANSFER CATALYST FOR USE IN THE SYNTHESIS OF POLYOL FATTY ACID POLYESTERS

[76] Inventors: Patrick J. Corrigan, 33 Dexter Park Blvd., Cincinnati, Ohio 45241; John K. Howie, 5958 Olive Branch Rd., Oregonia, Ohio 45054

[21] Appl. No.: 749,568

[22] Filed: Nov. 15, 1996

[51] Int. Cl.$^6$ .............................. A61K 31/70; C07H 1/00
[52] U.S. Cl. .............................. 514/23; 514/25; 536/18.5; 536/18.6; 536/115; 536/116; 536/119; 536/120; 536/124
[58] Field of Search ...................... 536/119, 124, 536/18.5, 18.6, 4.1, 115, 116, 120; 574/25, 23, 13

[56] References Cited

U.S. PATENT DOCUMENTS 3,963,699  6/1976  Rizzi ......................................... 536/119

OTHER PUBLICATIONS

Starks, et al., *Phase–Transfer Catalysis, Fundamentals, Applications, and Industrial Perspectives,* Chapters 1 and 2, Chapman & Hall, 1994.

*Kirk–Othmer Encyclopedia of Chemical Technology,* Third Edition, vol. 5, pp. 374–383, Catalysis, Phase–Transfer, 1979.

Stark, Charles, *Selecting a phase transfer catalyst,* Chemtech, pp. 110–117, Feb. 1980.

Brunelle, Daniel J., *Stable Catalysts for Phase Transfer at Elevated Temperatures,* Phase–Transfer Catalysis, New Chemistry, Catalysts, and Applications, Jul. 1986.

Dehmlow, Eckehard V., *Advances in Phase–Transfer Catalysis,* Angewandte Chemie, International Edition in English, vol. 16—No. 8, Aug. 1977, pp. 493–505.

Dehmlow, Eckehard V. et al., *Applications of Phase–transfer Catalysis,* Part 42. The Influence of Water Traces on Some Solid–Liquid Phase–transfer Catalysis Processes, J. Chem. Research, 1988, 384–385.

Dehmlow, Eckehard V. et al., *Applications of Phase–transfer Catalysis,* Part 47. Relative Stabilities ans Performances of Various Phase Transfer Catalysts, J. Chem Research, 1989, 224–225.

Bram et al, "Organic Synthesis Without Solvent: Base–Catalysed Ester Interchange," *Tetrahedron Letters,* 29: 4567–8 (1988).

Chemical Abstract 120:5480g (1994).

Chemical Abstracts 120:54821h (1994).

Wang, et al., Synthesis of Sucrose Esters by Phase–Transfer Catalysts, Journal of Huagiao University (Natural Science), 12(4):450–454 Oct., 1991 (English translation).

*Primary Examiner*—Elli Peselev

[57] ABSTRACT

A reaction mixture for manufacturing polyol fatty acid polyesters comprises a polyol, a fatty acid lower alkyl ester, a base initiator and a phase transfer catalyst. The phase transfer catalyst can be a quaternary ammonium compound, a crown ether, a polyethylene glycol, a polyethylene glycol ether, a polyethylene glycol ester or mixtures thereof. The process of making polyol fatty acid polyesters is carried out at low temperatures and essentially in the absence of a solvent or emulsifier. The polyol fatty acid polyester product stream produced by the foregoing process and reaction mixture has a lower concentration of reaction by-products such as di-fatty ketones and beta-ketoesters and of caramelized by-product which results from the breakdown of the polyol reactant.

36 Claims, 1 Drawing Sheet

PHASE TRANSFER CATALYST FOR USE IN THE SYNTHESIS OF POLYOL FATTY ACID POLYESTERS

TECHNICAL FIELD

This invention relates to phase transfer catalysts for use in the synthesis of polyol fatty acid polyesters. Additionally, this invention relates to methods of synthesizing polyol fatty acid polyesters in an essentially solvent free, low temperature reaction using quaternary ammonium compounds, crown ethers, polyethylene glycols, polyethylene glycol ethers, polyethylene glycol esters or mixtures thereof as phase transfer catalysts. The phase transfer catalysts of the present invention allow the polyol fatty acid polyesters to be synthesized in the absence of a solvent at relatively low temperatures which reduces the degradation of the polyol feed stream, thus, resulting in a product with higher purity and a higher concentration of the desired polyol fatty acid polyester.

BACKGROUND OF THE INVENTION

Phase transfer catalysts are used in a wide variety of chemical processes where one or more phase boundaries exist and one or more constituents must cross a phase boundary. A phase transfer catalyst can take one reactant from its "normal" phase into the phase of the second reactant such that a reaction between the two can occur. For a phase transfer catalyst to be effective, it should deliver one reactant from its normal phase to the phase of another reactant such that the first reactant is in a reactive form. Following the reaction of the two constituents, the phase transfer catalyst should be regenerated, i.e., recomplexed with an anion, and then recycled to the first phase in order to catalyze the transfer of another reactant.

Although a wide variety of phase transfer catalysts are known and used in the chemical industry, certain phase transfer catalysts work more effectively than others for a particular chemical reaction and for individual reactants. Thus, choosing a phase transfer catalyst can be a critical factor in the design of a reaction process and the reaction equipment, and in selection of the reaction constituents.

The primary function of a phase transfer catalyst is to move an ion in a reactive state from one phase to a second phase. It is believed that a phase transfer catalyst performs a true catalytic function by first disassociating from its anion, associating with a different anion in the first phase, and carrying the anion in a reactive state across the phase boundary between the first and second phase. After the ion reacts with a constituent in the second phase, the phase transfer catalyst reassociates with an anion and returns to the first phase in its original form to catalyze another phase transfer.

Alternatives to phase transfer catalysts include emulsifiers and solvents. It is believed that emulsifiers physically surround one reactant, i.e., form micelles or inverted micelles, and physically transport the first reactant to the second reactant, thus, allowing the two reactants to come into physical contact and to chemically react. Solvents work by dissolving both reactants into one phase so that the two reactants can physically contact one another and chemically react. However, it is often difficult to find a solvent in which all chemical reactants are soluble, and which is compatible with both the reactants and the desired product.

In the case of both solvents and emulsifiers, significant quantities of a non-reacting species, i.e., inerts, must be added to the reaction mixture and typically these non-reacting species must later be removed. The separation of undesirable species can be both expensive and time consuming. Additionally, removal or separation processes are almost never perfect and, thus, residual amounts of the solvents and/or emulsifier will be left in the reaction product and some valuable product is often removed during the separation process.

Additionally, the solvent or emulsifier should be compatible with the reaction mixture and, more importantly, compatible in the reaction product's final use. For example, dimethylformamide (DMF) is a good solvent and can be used to react a variety of substances which are soluble in either water or organics, but not both. However, DMF is a suspected carcinogen. Hence, if the reaction product is to be used as a food source, the use of DMF as a solvent in the reaction process is inappropriate because residual amounts of DMF are likely to be present in the final product.

The production of polyol fatty acid polyesters for use as a food additive has generated considerable interest in recent times. The transesterification of a polyol to produce a polyol fatty acid polyester has been conducted with both solvents and emulsifiers. However, in order for the transesterification reaction to proceed at an appreciable rate when using an emulsifier, i.e., in a solventless system, relatively high temperatures, i.e., over 125° C. are generally required. The polyol, which can be, for example, a monosaccharide, a disaccharide or a sugar alcohol, often begins to degrade at these relatively high temperatures and forms a caramelized by-product which does not productively participate in the transesterification reaction. Thus, the reaction product includes not only the desired polyol polyester and the generally undesirable emulsifier, but also the caramelized by-product of the broken down polyol. For example, sucrose, a common polyol, begins to degrade appreciably at 130° C., and is completely degraded at 180° C. Thus, at the completion of the transesterification reaction, the desired polyol fatty acid polyester must be separated not only from the emulsifier but also from the caramelized by-product. This often adds significant expense and processing time to the manufacturing process.

Additionally, when the transesterification reaction is conducted in the presence of a solvent and/or an emulsifier, an increase in the production of lower di-fatty ketones and beta-ketoesters often results. The lower di-fatty ketones and beta-ketoesters are reaction by-products of the transesterification of a polyol. As with the caramelized by-product of the polyol reactants, the lower di-fatty ketones and beta-ketoesters are generally undesirable and it is often required that these by-products be removed from the product stream before the product is suitable for use in various applications. However, operating a transesterification reaction at lower temperatures and eliminating the solvent and/or the emulsifier reduces the production of lower di-fatty ketones and beta-ketoesters significantly, often by an order of magnitude. Thus, additional separation costs and processing time which are incurred when solvents and/or emulsifiers are used, are avoided when a phase transfer catalyst is employed in the manufacture of polyol fatty acid polyester by transesterification of a polyol.

There is therefore a continuing need to provide a process for manufacturing polyol fatty acid polyesters in a low temperature, solventless process through the use of a phase transfer catalyst. Additionally, it is desirable to provide a reaction mixture which comprises a polyol, a fatty acid lower alkyl ester, a base catalyst and a phase transfer catalyst for use in a low temperature solventless transesterification reaction to produce a superior polyol fatty acid polyester product stream.

SUMMARY OF THE INVENTION

Accordingly, it is an object of the present invention to provide an improved phase transfer catalyst for manufacturing polyol fatty acid polyesters, and, more particularly, it is an object of the present invention to provide an improved process for manufacturing polyol fatty acid polyesters through the transesterification of a polyol in the presence of a phase transfer catalyst.

It is a related object of the present invention to provide a reaction mixture of a phase transfer catalyst, a fatty acid lower alkyl ester, a base initiator and a polyol for use in a low temperature transesterification reaction to produce a polyol fatty acid polyester. Additionally, an improved reaction product of polyol fatty acid polyester is provided which is a product of the reaction mixture and the low temperature process of the present invention.

These and additional objects are provided by the present invention. Specifically, the invention, in one embodiment, is directed to an essentially solvent-free low temperature mixture of a phase transfer catalyst, a polyol, a fatty acid lower alkyl ester, and a base initiator. In a preferred embodiment, the phase transfer catalyst is a quaternary ammonium compound, a crown ether such as an 18-C-6 crown ether, a polyethylene glycol, a polyethylene glycol ether, a polyethylene glycol ester or a mixture thereof. Preferably, the solvent-free low temperature mixture is used in a transesterification reaction at low temperature to produce a polyol fatty acid polyester. The reaction is preferably carried out at a temperature below about 125° C. and more preferably below about 110° C., whereby high temperature degradation of the polyol is substantially avoided. In a more preferred embodiment, the phase transfer catalyst is a quaternary ammonium compound and the associated anion is stearate or bromide and the total number of carbon atoms associated with the quaternary ammonium compound is from 12 to 24 and more preferably from about 16 to about 20 carbon atoms.

In another preferred embodiment, the invention is directed to a low temperature, essentially solvent free process for producing a polyol fatty acid polyester and an improved polyol fatty acid polyester product stream. A mixture of a polyol, a fatty acid lower alkyl ester, a phase transfer catalyst and a base initiator is heated at low temperature to produce the polyol fatty acid polyester. In a preferred process, the phase transfer catalyst is a quaternary ammonium compound, a crown ether such as an 18-C-6 crown ether, a polyethylene glycol, a polyethylene glycol ether, a polyethylene glycol ester or a mixture thereof. In an especially preferred process, the phase transfer catalyst is a quaternary ammonium compound wherein the anion is a stearate or bromide ion. In an especially preferred process, essentially no solvent is used and the reaction is carried out at a temperature below about 125° C. and preferably below about 110° C.

The process, reaction mixture, and product stream of the present invention allow polyols to be transesterified in the absence of a solvent or an emulsifier at a reduced temperature and result in less degradation of the polyol reactant and decreased formation of undesirable by-products. This provides a product stream with a higher concentration of the desired polyester product and higher purity, i.e., significantly lower concentrations of caramelized by-product, di-fatty ketones and beta-ketoesters as compared with conventional processes. The present invention therefore results in lower separation costs, and lower waste disposal costs in the production of polyol fatty acid polyesters.

DETAILED DESCRIPTION

Figure 1:
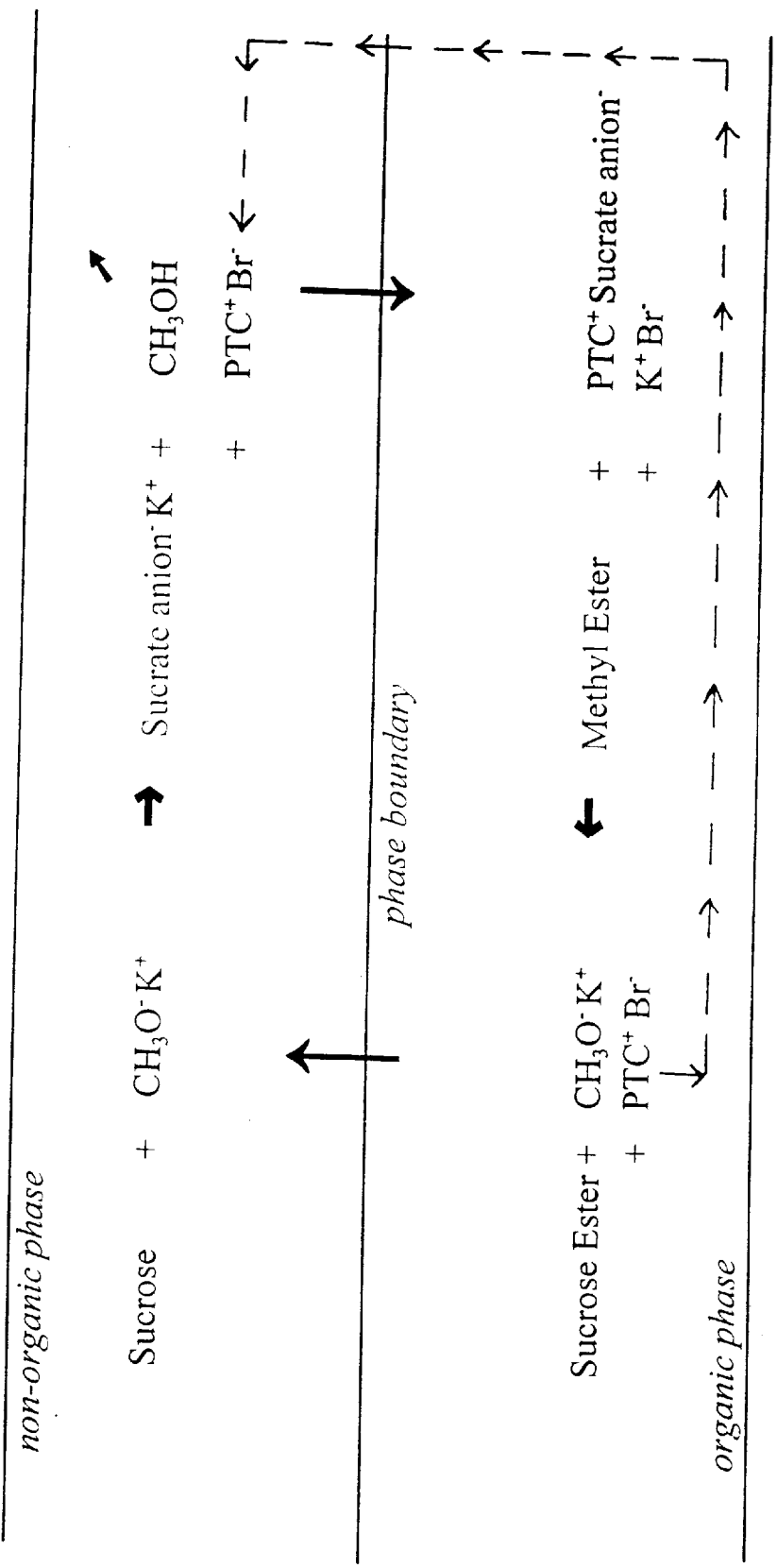
FIG. 1 is a schematic depiction of an essentially solvent free reaction mixture in accordance with one aspect of the present invention.

The present invention will now be described in detail with reference to specific embodiments. In accordance with the present invention, to produce a polyol fatty acid polyester, polyols are reacted with fatty acid lower alkyl esters in the presence of a base initiator and a phase transfer catalyst. The polyol fatty acid polyester can be used in, among other things, a food additive.

As used herein, the term "polyol" is intended to include any aliphatic or aromatic compound containing at least two free hydroxyl groups. For example, suitable polyols may be selected from the following classes: saturated and unsaturated, straight and branched chain, linear aliphatics; saturated and unsaturated, cyclic aliphatics including heterocyclic aliphatics; or mononuclear and polynuclear aromatics including heterocyclic aromatics.

Preferred polyols for use in the reaction mixture and process described herein include monosaccharides, disaccharides, sugar alcohols and mixtures thereof. Accordingly, monosaccharides suitable for use herein include, for example: glucose, mannose, galactose, arabinose, xylose, ribose, abiose, rhamnose, psicose, fructose, sorbose, tagintose, ribulose, xylulose, and erythrulose. Disaccharides suitable for use herein include, but are not limited to, maltose, cellobiose, lactose, and sucrose. The sugar alcohols most widely distributed in nature and suitable for use are sorbitol, mannitol, and galactitol. Especially preferred polyols for use herein include xylitol, sorbitol, and sucrose. Sugar ethers as well as alkoxylated glycerols or glycols can also be used.

A base initiator, also known as a basic catalyst is generally used to increase the rate of reaction for the transesterification of a polyol to form a polyol fatty acid polyester. A discussion of types of basic catalysts and their function in the transesterification of polyols can be found in U.S. Pat. No. 3,963,699 to Rizzi et al., the entire disclosure of which is incorporated herein by reference. Specifically, basic catalysts are discussed at column 4, lines 12–19 of the Rizzi et al. reference. It should be understood that while the reaction mixtures, process, and the product stream are described herein in conjunction with the use of a basic catalyst, other alternative reaction mixtures and processes are within the scope of the invention, but are generally not preferred. The basic catalyst is typically a strong base with an affinity for hydrogen and is often referred to as a base initiator because it serves to transform the polyol from a stable molecule to a reactive ion. Thus, the terms "basic catalyst" and "base initiator" are interchangeable as used herein. Specifically, the basic catalyst removes a hydrogen from the polyol molecule resulting in a polyol ion in a reactive state. For example, the basic catalyst converts sucrose to sucrate ion. Preferred basic catalysts are carbonate and methoxide ions, which can be complexed with an alkali or alkaline earth metal, for example, potassium or sodium. If sucrose is the polyol and potassium methoxide is the basic catalyst, the methoxide ion removes a hydrogen from the sucrose molecule resulting in the formation of methanol and a sucrate ion which is loosely bound with the potassium cation. This reaction is illustrated in FIG. 1 in the non-organic phase. It is the sucrate anion which reacts with the phase transfer catalyst, whereby the phase transfer catalyst pulls the sucrate ion from the non-organic phase into the organic phase where it can react with the fatty acid lower alkyl ester, as is further illustrated in FIG. 1 in the organic phase, and as is described in greater detail below.

As used herein, the term "phase transfer catalyst" is intended to include all chemical species which can react with another chemical species to form a chemical complex, wherein the complexed species can travel from one phase to a second phase, and wherein the individual chemical species prior to complexing would not normally be soluble in the second phase. A phase transfer catalyst, as described herein, is to be distinguished from an emulsifier, e.g., a fatty acid soap, in that an emulsifier is believed to provide a single phase or emulsified system in which both chemical species are soluble, i.e. without the need for chemical complexing.

As will be apparent, in the transesterification of a polyol to form a polyol fatty acid polyester, the phase transfer catalyst is regenerated after transporting a reactant from one phase to another such that the phase transfer catalyst is available to catalyze another phase transfer. The phase transfer catalyst moves from one phase to another but is generally not consumed in the reaction. However, due to side reactions which occur simultaneously with the transesterification reaction, (although generally less frequently or at a significantly slower rate), the phase transfer catalyst is sometimes degraded or transformed into chemical species which do not perform the phase transfer function. Thus, the product stream will generally comprise the desired product, residual phase transfer catalyst, the degradation by-products of the phase transfer catalyst, unreacted initial reactants and by-products of the initial reactants.

While not intending to be limited to any particular theory and/or reactant, FIG. 1 illustrates an exemplary phase transfer reaction. FIG. 1 shows a reaction mixture in three phases (solid, non-organic, and organic) resulting from an initial mixture of a polyol, a base initiator, a phase transfer catalyst and a fatty acid lower alkyl ester. The non-organic phase contains a solid sucrose particle (the polyol), potassium methoxide (the base initiator), and the phase transfer catalyst. The organic phase contains a fatty acid methyl ester, i.e., the fatty acid lower alkyl ester. At the exterior of the sucrose particle are sucrose molecules which react with the base initiator, i.e., the basic catalyst which in this example is potassium methoxide. The methoxide ion removes a hydrogen atom from the sucrose molecule forming a sucrate anion and methanol. The methanol may be removed from the reaction mixture. The sucrose molecule is thus changed to a sucrate anion which is loosely bound to the potassium cation. The sucrate ion is in a form which can bind with quaternary ammonium ion, crown ether ion, or ions of polyethylene glycols, polyethylene glycol ethers, or polyethylene glycol esters, i.e., the phase transfer cation.

After the sucrate anion and phase transfer catalyst cation are associated, they transfer from the non-organic phase to the organic phase, whereby the sucrate ion is in the same phase as the fatty acid lower alkyl ester, i.e., the methyl ester in FIG. 1. The methyl ester reacts with the sucrate anion to form a sucrose ester and a methoxide ion which complexes with the potassium ion. The phase transfer catalyst cation then re-complexes with its anion, i.e., bromide in FIG. 1, thus regenerating the phase transfer catalyst so that it can travel back to the non-organic phase to catalyze another phase transfer. Likewise, the potassium cation associates with the methoxide ion which was generated as a by-product of the esterification of the sucrose. The methoxide ion travels back to the non-organic phase to initiate another sucrose molecule. The esterified sucrose molecule remains in the organic phase for further esterification.

Although the reaction mixtures and processes described herein are generally considered solventless, the term solventless is meant to indicate the presence of more than one phase. A "solventless" system may contain up to about 1.0% by weight solvents, but preferably less than about 0.1% by weight solvents. Organic solvents may be used in the organic phase, but their use is generally not preferred because they might have to be separated from the product stream. Appropriate solvents for use with the reaction mixtures described herein are hexane, methanol, or DMF.

It is believed that the phase transfer ion performs a true catalytic function by first disassociating from its anion, associating with the polyol ion, and carrying the polyol ion in a reactive state across the phase boundary to the fatty acid lower alkyl ester. After the polyol ion reacts with the fatty acid lower alkyl ester, the phase transfer catalyst reassociates with an anion and returns to the non-organic phase in its original form to catalyze another phase transfer. On the other hand, while not wanting to be restricted to any one theory, it is believed that the base initiator (i.e. the "basic catalyst") initiates the reaction of the polyol molecule to the sucrate ion but is itself transformed into lower alkyl alcohol which may be removed from the reaction mixture, and is no longer in a state to initiate another polyol molecule. During the esterification of the polyol ion, a lower alkyl ion in the form of an alcohol is removed from the fatty acid lower alkyl ester and a new base initiator is created which travels into the non-organic phase to initiate another polyol molecule.

Phase transfer catalysts which are appropriate for use in the transesterification of a polyol to form a polyol fatty acid polyester include quaternary salts, crown ethers polyethylene glycols, polyethylene glycol ethers, polyethylene glycol esters or mixtures thereof. The quaternary salts are of the general formula:

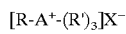

wherein

A is nitrogen or phosphorous,

R is a straight chain $C_1$–$C16$ hydrocarbon, each $R^1$ is individually a straight chain $C_{1-C8}$ hydrocarbon, and X is Cl, Br, I, or $C_2$–$C_{22}$ fatty acid ion.

A is preferably nitrogen because the polyol fatty acid polyesters produced by the reactions described herein are often used as food additives. The ammonium compounds are generally more compatible with a food product than is a phosphorous based phase transfer catalyst but, as can be appreciated, a polyester being produced for other uses could be catalyzed by the use of a phosphorous-based catalyst. The associated anion can be chloride, bromide, iodide or $C_2$–$C_{22}$ fatty acid ion, although bromide and stearate ions are especially preferred. The R and R' groups associated with the ammonium compound are preferably straight chain $C_1$–$C_{16}$ hydrocarbons. Especially preferred are straight chain $C_1$–$C_8$ hydrocarbons. It is generally believed that longer hydrocarbon chains provide better solubility in the organic phase, i.e., the phase transfer function is enhanced, however, the longer chains decrease the quaternary ammonium compound's propensity to react with the polyol ion due to the steric hindrance caused by the longer hydrocarbon chains. Thus, there is an optimization consideration when selecting a quaternary ammonium phase transfer catalyst wherein the molecule should be selected to be both readily soluble in the organic phase and reactive with the polyol ion.

Tetrabutyl ammonium compounds are especially preferred phase transfer catalysts for the transesterification of a polyol to form a polyol fatty acid polyester. The total number of carbon atoms in tetrabutyl ammonium compounds is 16. The preferred range of carbon atoms associated with a quaternary ammonium phase transfer catalyst is from about 12 to about 24 and an especially preferred range is from about 16 to about 20. Quaternary ammonium compounds are commercially available and often contain three hydrocarbon chains of one size with the fourth chain being slightly longer or shorter as is described by the chemical structure above, (i.e., R and (R')$_3$).

Crown ethers are also suitable phase transfer catalysts for use in the reactions described herein. Crown ethers are cyclic polyethers and preferred crown ethers are the 18-crown-6 ethers of the general formula $C_{12}H_{24}O_6$, i.e., hexaoxacyclooctadecane, and its derivatives. Preferred derivatives include the dicyclohexyl-18-crown-6 and dibenzo-18-crown-6, i.e. dicyclohexylhexaoxacyclooctadecane and dibenzohexaoxacyclooctadecane respectively. Crown ethers are generally known to the art and it is understood that other derivatives of 18-crown-6 and other crown ethers are also suitable for use in the reactions described herein. While not wanting to be restricted to any one theory, it is believed that a crown ether operates by attracting a cation, e.g., potassium, to the center of the crown, i.e., the approximate midpoint between the oxygen molecules in the cyclic structure. Having attracted the cation, and assuming a slightly positive charge, it is believed that the crown ether operates its phase transfer catalyst function in a manner similar to the quaternary ammonium catalyst structures described above.

Polyethylene glycols, polyethylene glycol ethers and polyethylene glycol esters (collectively know as "PEGs") are also suitable phase transfer catalysts for use in the reactions described herein. These substances are polyethers having the general formula:

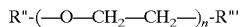

$$R''-(-O-CH_2-CH_2-)_n-R'''$$

wherein R" and R"' individually are hydrogen, an alkyl group of one or more carbon atoms, preferably from about 1 to about 20 carbon atoms and more preferably from about 1 to about 4 carbon atoms, or an esterified carboxylic acid such as fatty acids with carbon chains of from about 8 carbon atoms to about 22 carbon atoms, and wherein n is from about 2 to about 100, and preferably from about 4 to about 20. Preferably, PEGs for use in the present invention have a molecular weight within the range of from about 100 to about 5,000.

PEGs have a structural similarity to many crown ethers in that they are composed of ethylene oxide structural units. More particularly, PEGs contain two or more ether linkages which are believed to act as the functional components as discussed below, although Applicants do not intend to be bound by this theory. PEGs have the advantage of being less toxic and of lower cost than crown ethers. While not wanting to be restricted to any one theory, it is believed that, like crown ethers, PEGs operate by attracting a cation, e.g., potassium, to the ether linkages in the PEGs, thus catalyzing phase transfer. The resulting positively charged complex acts as a phase transfer catalyst similar to the crown ether complexes.

PEGs can be incorporated into the reaction mixtures described herein in concentrations of from about 0.5% to about 20% by weight, and preferably from about 5% to about 15% by weight. In one embodiment of the present invention, a reaction mixture can be made comprising a phase transfer catalyst, a polyol, a fatty acid lower alkyl ester and a base initiator with essentially no solvents or emulsifiers. The phase transfer catalyst can be present in amounts of as little as 0.5% by weight, based the total weight of the reaction mixture, and still provide significantly improved esterification by catalyzing phase transfer. The transesterification reaction is generally thought to be pseudo first order with respect to phase transfer catalyst concentration. Thus, a higher concentration of phase transfer catalyst generally results in a faster transesterification reaction. However, it is often necessary to remove the phase transfer catalyst from the product stream, thus, minimizing the amount of catalyst added also minimizes the amount that must be later removed and therefore reduces separation costs. To produce the desired polyesters a molar ratio of the polyol to the fatty acid lower alkyl ester is generally in the range of 1:8 to 1:16 and more preferably in the range of 1:10 to 1:12.

For the solventless transesterification reaction of the polyol and the fatty acid lower alkyl ester to occur at an appreciable rate, it is generally preferred that the reaction mixture described herein be heated, preferably to a temperature of about 125° C. or below. Agitation is also preferable, although as can be appreciated, agitation is relative to the volume and design of each reaction vessel. Heating the reaction mixture to about 110° C. or below is an especially preferred method of carrying out the reaction of the polyol with the fatty acid lower alkyl ester. When the transesterification reaction is carried out at temperatures of about 125° C. or below, the polyol reactant is generally broken down, if at all, at a significantly slower rate when compared to reactions which occur at higher temperatures, resulting in significantly less caramelized by-product in the final product stream.

Reducing the formation of degradation by-products of the polyol is an important goal of the present invention for a variety of reasons. All polyol that is degraded, i.e., caramelized, is unavailable to react to form sucrose polyester, resulting in a lower yield of the desired product. Additionally, the caramelized by-product is generally considered an impurity in the product stream and to produce a relatively pure product, the caramelized polyol must be removed. Likewise, the di-fatty ketones and beta-ketoesters discussed above, i.e., reaction by-products, are also generally considered impurities and their removal is often desirable. Removing these unwanted constituents from the product stream often requires additional separation equipment, time and ultimately cost for the polyol fatty acid polyester manufacturing process. For example, filtering and "washing" the product stream often requires silica, surfactants, solvents and water, all of which may be increased in quantity as the concentration of impurities increases. Also, once the caramelized by-product, di-fatty ketones, and beta-ketoesters have been removed, they must be disposed of which increases disposal cost and adds additional cost to the manufacturing process. Finally, in general, separation processes often remove some of the desired product stream along with the undesirable by-products, e.g., the caramelized by-product of the polyol reactant. This results in the loss of valuable product.

The product stream which results from the reaction mixture and the process described above, is superior in color, viscosity, clarity and concentration of the desired product. Caramelized by-product of a polyol is generally a brown, i.e., caramel, color which, depending on the concentration in the product stream, tends to at least turn the product cloudy and often turns the product a dark brown color. By reducing the concentration of the caramelized by-product through the use of the reaction mixture and processes described herein, the reaction product is more clear. The product stream is generally less viscous due to the lower concentration of the caramelized by-product and soap that forms when the sucrose degrades and thus, the product stream is generally easier to process. Also, because less of the initial polyol is degraded through the use of the reaction mixture and reaction process described herein, more polyol is available to be transesterified. This results in a higher concentration of the desired polyester product when compared to similar reaction conditions run with a solvent or an emulsifier at higher temperatures. Additionally, substantially all of said polyol fatty acid polyester molecules contain at least two or more fatty acid esters per molecule following the transesterifcation reactions described herein. Wherein "substantially all" is intended to mean greater that about 98% of the sucrose molecules contain two or more fatty acid esters.

The Detailed Description above will be better understood when read in conjunction with the following examples wherein the following reaction mixtures are made and reacted to form the product stream having the concentrations tabulated at the end of each example.

Example 1

A reaction mixture of about 34.2 grams of sucrose, about 2.8 grams of potassium carbonate, about 25 grams of potassium stearate (soap), and about 300 grams of cottonseed fatty acid methyl esters is prepared and added to a 1-liter glass reaction vessel. The reaction vessel is equipped with a heating mantle, a thermocouple, a temperature controller, a nitrogen sparging tube that extends below the liquid level, an agitator, and a sample port. The reaction mixture is heated to about 135° C., while being agitated and sparged with nitrogen. At the end of about 6 hours of heating at about 135° C., a sample is taken from the reactor and analyzed for composition. The approximate sample composition is shown below.

| | |
|---|---|
| Sucrose octaester | 67% |
| Sucrose heptaester and lower sucrose esters | 11% |
| Unreacted methyl esters | 11% |
| Soaps | 8% |
| Unreacted sucrose | 0.5% |
| Sucrose decomposition products | 2% |
| Other | 0.5% |

A mass balance of the reaction mixture and the above product stream indicates that about 20% of the starting sucrose decomposed during the course of the reaction. The color of the product is opaque dark brown, and the viscosity of the product is about 30 centipoise. The combined level of di-fatty ketone and beta-ketoester is about 365 parts per million by weight. Thus, a typical solventless sucrose polyester reaction run at 135° C., using an emulsifier, produces a product with a high level of sucrose decomposition and a high level of di-fatty ketone.

Example 2

A reaction similar to the reaction described in Example 1 is conducted at 110° C. instead of 135° C. At the end of 6 hours there is no detectable sucrose ester of any type in the reaction mixture. Hence, a conventional solventless sucrose polyester reaction using an emulsifier will not react substantially at 110° C.

Example 3

A reaction similar to Example 1 is conducted, except no potassium stearate is added, and in place of the soap about 2 grams of tetrabutyl ammonium stearate is added to the reaction mixture. The mixture is reacted at about 110° C. (instead of 135° C. as used in Example 1) for about 6 hours. At the end of about 6 hours, a sample is taken from the reactor and its composition analyzed. The approximate composition of the sample is shown below.

| | |
|---|---|
| Sucrose octaester | 44% |
| Sucrose heptaester and lower sucrose esters | 33% |
| Unreacted methyl esters | 22% |
| Soaps | 0 |
| Unreacted sucrose | 3% |
| Sucrose decomposition products | 0 |
| Other | 1% |

A mass balance of the reaction mixture and the product stream tabulated above indicates that 0% of the staring sucrose decomposed during the course of the reaction. The color of the product stream is light yellow, and the viscosity of the product is about 15 centipoise. The combined level of di-fatty ketone and beta-ketoester is about 25 parts per million. This example demonstrates that a solventless sucrose polyester reaction can be run in the absence of an emulsifier at 110° C. when using a phase transfer catalyst and can achieve a high degree of completion, low sucrose decomposition, and low di-fatty ketone levels.

Example 4

A reaction similar to Example 1 is conducted, except no potassium stearate is added, and in place of the soap about 5 grams of didodecyldimethyl ammonium bromide is added to the reaction mixture. The mixture is reacted at about 110° C. (instead of 135° C. as used in Example 1) for about 2 hours. At the end of about 2 hours, the reaction mixture is filtered to remove the unreacted sucrose and didodecyldimethyl ammonium bromide, then returned to the reactor along with about 2 drops of potassium methoxide solution (25% potassium methoxide in methanol). The mixture is heated to 110° C., agitated and sparged with nitrogen for an additional 2 hours. At the end of about 2 hours, a sample is taken from the reactor and its composition analyzed. The approximate sample composition is shown below.

| | |
|---|---|
| Sucrose octaester | 69% |
| Sucrose heptaester and lower sucrose esters | 10% |
| Unreacted methyl esters | 19% |
| Soaps | 0 |
| Unreacted sucrose | 0 |
| Sucrose decomposition products | 0 |
| Other | 1% |

A mass balance of the reaction mixture and the product stream indicates that 0% of the starting sucrose decomposed during the course of the reaction. The color of the product is light yellow, and the viscosity of the product is about 15 centipoise. Thus, a solventless sucrose polyester reaction can be run in the absence of an emulsifier at 110° C. when using a phase transfer catalyst.

Example 5

A reaction similar to Example 1 is conducted, except that about 20 grams of polyethylene glycol 900 is added in addition to about 20 grams of potassium stearate to the reaction mixture. The mixture is reacted at about 110° C. (instead of 135° C. as used in Example 1) for about 7 hours. At the end of about 7 hours, a sample is taken from the reactor and analyzed for composition. The approximate sample composition is shown below.

| | |
|---|---|
| Sucrose octaester | 19% |
| Sucrose heptaester and lower sucrose esters | 24% |
| Unreacted methyl esters | 49% |
| Soaps | 0 |
| Unreacted sucrose | 3% |
| Sucrose decomposition products | 0 |
| Polyethylene glycol esters | 5% |

This example demonstrates that a solventless sucrose polyester reaction can be run at 110° C. when using polyethylene glycol 900 as a phase transfer catalyst in the presence of an emulsifier.

Example 6

This example demonstrates the use of a phase transfer catalyst in a continuous reaction system, wherein a high degree of esterification is achieved. The continuous reaction system consists of two sections of glass pipe, each approximately 6 inches in diameter and 48 inches long, the sections are connected in series. Fourteen plates are placed in each column at equal intervals dividing each column into sections. Each plate has a hole in the center about 1 inch in diameter. Each section has a 6-blade turbine type agitator, operated at about 500 RPM. The agitator diameter is approximately one-half the diameter of the column. A heating mantle with a temperature controller surrounds the outside of each column. A reaction mixture consisting of about 1000 grams of sucrose, 82 grams of potassium carbonate, about 8772 grams of cottonseed fatty acid methyl esters, and about 146 grams of tetrabutyl ammonium stearate is mixed in an agitated feed tank which is also heated. The molar ratio of cottonseed methyl esters to sucrose is about 11:1. There is no potassium stearate in this example.

The reaction mixture is continuously pumped from the feed tank into the top of the reaction column at about 44 grams per minute. The reaction mixture flows downward by gravity from the top section of the column to the lower section of the column. Nitrogen is introduced at the bottom of the column and travels upward through the column, through the center holes and counter current to the liquid flow. In each segment, the nitrogen is dispersed into the liquid by the agitators to produce very small bubbles, approximately 2 mm in average diameter. The nitrogen strips the methanol by-product from the reaction mixture, and proceeds upward through the column (propelled by buoyant forces), from section to section. The partial pressure of methanol in the nitrogen gas in the bottom section of the column is about 1 mm Hg. The nitrogen is exhausted from the column when it reaches the top.

The partially reacted product from the first column is pumped from the bottom of the first column, through a filter to remove residual unreacted sucrose, then to the top of the second column. The material from the first column flows downward by gravity through the second column. Nitrogen enters the bottom of the second column and travels upward through the center holes counter current to the liquid flow. In each segment, the nitrogen is dispersed into the liquid by the agitators to produce very small bubbles, approximately 2 mm diameter average. The partial pressure of methanol in the nitrogen gas in the bottom section of the column is about 1 mm Hg.

Both reaction columns are operated at about 110° C., at about atmospheric pressure at the top of the column, and at about 0.5 psig above atmospheric pressure at the bottom of the column. The weight ratio of nitrogen to the incoming liquid feed is about 2:1 in each column, and the average residence time of the liquid in each column is about 3.5 hours, for a total residence time of 7 hours. This reaction gives a product stream which is a light yellow color, indicating no evidence of sucrose decomposition. The di-fatty ketone level is about 51 ppm. The product composition is shown below.

| | |
|---|---|
| Sucrose octaester | 38% |
| Sucrose heptaester and lower sucrose esters | 10% |
| Unreacted methyl esters | 62% |
| Soaps | 0 |
| Unreacted sucrose | trace |
| Sucrose decomposition products | 0 |

Thus, the reactions described herein can be run in a continuous reactor scheme as well as in a batch-type operation.

Having shown and described the preferred embodiments of the present invention, further adaptation of the reaction mixtures, processes and product streams for manufacturing a polyol fatty acid polyester through the use of a phase transfer catalyst can be accomplished by appropriate modifications by one of ordinary skill in the art without departing from the scope of the present invention. A number of alternatives and modifications have been described herein and others will be apparent to those skilled in the art. For example, this reaction can be effectively run in a batch reaction process or a continuous reaction process. Additionally, although specific phase transfer catalysts have been described, other catalysts can be used to produce the desired polyol fatty acid polyester. Likewise, while numerous polyols and fatty acid lower alkyl esters have been disclosed for the reaction mixture as preferred embodiments of the present invention, the constituents can be varied to produce other embodiments of the present invention as desired. Accordingly, the scope of the present invention should be considered in terms of the following claims and is understood not to be limited to the details of the compositions and methods shown and described in the specification.

I claim:

1. An essentially solvent free mixture of a phase transfer catalyst, a polyol, a fatty acid lower alkyl ester and a base initiator, wherein said phase transfer catalyst comprises:

a compound of the formula $(R-A^+-(R')_3)X^-$, a crown ether compound, a compound of the formula $R''-(-O-CH_2-CH_2-)_n-R'''$, or mixtures of said compounds;

wherein

A is nitrogen or phosphorous,

R is a straight chain $C_1-C_{16}$ hydrocarbon, each R' is individually a straight chain $C_1-C_8$ hydrocarbon, X is Cl, Br, I, or $C_2-C_{22}$ fatty acid ion, R" and R''' individually are hydrogen, an alkyl group of from about 1 to about 20 carbon atoms, or an esterified carboxylic acid, and n is from about 2 to about 100.

2. A mixture according to claim 1, wherein said mixture is maintained at a temperature not greater than about 125° C.

3. A mixture according to claim 1, wherein said mixture is maintained at a temperature not greater than about 110° C.

4. A mixture according to claim 1, wherein X is stearate and A is nitrogen.

5. A mixture according to claim 4, wherein R is butyl and each R' is butyl.

6. A mixture according to claim 1, wherein X is bromide and A is nitrogen.

7. A mixture according to claim 6, wherein R is butyl and each R' is butyl.

8. A mixture according to claim 1, wherein the total number of carbon atoms present in R and the three R' carbon chains is from about 12 to about 24.

9. A mixture according to claim 1, wherein the total number of carbon atoms present in R and the three R' carbon chains is from about 16 to about 20.

10. A mixture according to claim 1, wherein said crown ether is selected from the group consisting of hexaoxacyclooctadecane, dicyclohexylhexaoxacyclooctadecane, dibenzohexaoxacyclooctadecane, and mixtures thereof.

11. A mixture according to claim 1, wherein said compound of the formula R"-(—O—CH$_2$—CH$_2$—)$_n$-R'" has a molecular weight of from about 100 to about 5,000.

12. A mixture according to claim 1, wherein at least one of R" and R'" is hydrogen.

13. A mixture according to claim 1, wherein the polyol is selected from the group consisting of monosaccharides, disaccharides, sugar alcohols and mixtures thereof.

14. A mixture according to claim 1, wherein the polyol is a disaccharide.

15. A mixture according to claim 1, wherein the polyol is selected from the group consisting of sucrose, xylitol, sorbitol and mixtures thereof.

16. A mixture according to claim 1, wherein the base initiator is selected from the group consisting of potassium methoxide, potassium carbonate, sodium methoxide, sodium carbonate and mixtures thereof.

17. A mixture according to claim 1, wherein the fatty acid lower alkyl ester is a fatty acid methyl ester.

18. A solvent-free process for synthesizing polyol fatty acid polyesters comprising the steps of:
   i) mixing a polyol with a fatty acid lower alkyl ester in the presence of a phase transfer catalyst, and
   ii) heating said mixture to react said polyol with said fatty acid lower alkyl ester to form polyol fatty acid polyester, wherein substantially all of said polyol fatty acid polyester molecules contain at least two or more fatty acid esters per molecule.

19. A solvent-free process for synthesizing polyol fatty acid polyesters comprising the steps of:
   i) mixing a polyol with a fatty acid lower alkyl ester in the presence of a phase transfer catalyst, and
   ii) heating said mixture to react said polyol with said fatty acid lower alkyl ester to form polyol fatty acid polyester, wherein substantially all of said polyol fatty acid polyester molecules contain at least two or more fatty acid esters per molecule;
wherein said phase transfer catalyst comprises:
   a compound of the formula (R-A$^+$-(R')$_3$)X$^-$, a crown ether compound, a compound of the formula R"-(—O—CH$_2$—CH$_2$—)$_n$-R'", or mixtures of said compounds;
wherein
A is nitrogen or phosphorous, R is a straight chain C$_1$-C$_{16}$ hydrocarbon,
each R' is individually a straight chain C$_1$-C$_8$ hydrocarbon,
X is Cl, Br, I, or C$_2$-C$_{22}$ fatty acid ion, R" and R'" individually are hydrogen, an alkyl group of from about 1 to about 20 carbon atoms, or an esterified carboxylic acid, and
n is from about 2 to about 100.

20. A process according to claim 18, wherein said polyol and said fatty acid lower alkyl ester are reacted at a temperature not greater than about 125° C.

21. A process according to claim 18, wherein said polyol and said fatty acid lower alkyl ester are reacted at a temperature not greater than about 110° C.

22. A process according to claim 19, wherein X is stearate and A is nitrogen.

23. A process according to claim 22, wherein R is butyl and each R' is butyl.

24. A process according to claim 19, wherein X is bromide and A is nitrogen.

25. A process according to claim 24, wherein R is butyl and each R' is butyl.

26. A process according to claim 19, wherein the total number of carbon atoms present in R and the three R' carbon chains is from about 12 to about 24.

27. A process according to claim 19, wherein the total number of carbon atoms present in R and the three R' carbon chains is from about 16 to about 20.

28. A process according to claim 19, wherein said crown ether is selected from the group consisting of hexaoxacyclooctadecane, dicyclohexylhexaoxacyclooctadecane, dibenzohexaoxacyclooctadecane, and mixtures thereof.

29. A process according to claim 19, wherein said compound of the formula R"-(—O—CH$_2$—CH$_2$—)$_n$-R'" has a molecular weight of from about 100 to about 5,000.

30. A process according to claim 29, wherein at least one of R" and R'" is hydrogen.

31. A process according to claim 18, wherein the polyol is selected from the group consisting of monosaccharides, disaccharides, sugar alcohols and mixtures thereof.

32. A process according to claim 31, wherein the polyol is a disaccharide.

33. A process according to claim 18, wherein the polyol is selected from the group consisting of sucrose, xylitol, sorbitol and mixtures thereof.

34. A process according to claim 18, wherein the mixture further comprises a base initiator selected from the group consisting of potassium methoxide, potassium carbonate, sodium methoxide, sodium carbonate and mixtures thereof.

35. A process according to claim 18, wherein the fatty acid lower alkyl ester is a fatty acid methyl ester.

36. A process according to claim 18, wherein the molar ratio of the polyol to the fatty acid lower alkyl esters is in the range of from 1:8 to 1:16.

\* \* \* \* \*